United States Patent [19]

Marquis

[11] Patent Number: 6,015,550

[45] Date of Patent: Jan. 18, 2000

[54] METHOD FOR CONTROLLING ODOR USING ALKYLENE CARBONATES

[75] Inventor: Edward T. Marquis, Austin, Tex.

[73] Assignee: Huntsman Petrochemical Corporation, Austin, Tex.

[21] Appl. No.: 09/010,925

[22] Filed: Jan. 22, 1998

Related U.S. Application Data

[60] Provisional application No. 60/035,980, Jan. 22, 1997.

[51] Int. Cl.$^7$ .......................................................... A61L 9/04
[52] U.S. Cl. .................... 424/76.1; 424/76.2; 424/76.21; 424/76.5; 424/76.6; 424/76.7
[58] Field of Search ................................ 424/76.1, 76.2, 424/76.21, 76.5, 76.6, 76.7

[56] References Cited

U.S. PATENT DOCUMENTS

| | | | |
|---|---|---|---|
| 5,098,594 | 3/1992 | Doscher | 252/162 |
| 5,736,496 | 4/1998 | Durbut et al. | 510/235 |
| 5,772,722 | 6/1998 | Gednalske et al. | 71/21 |

*Primary Examiner*—S. Mark Clardy
*Assistant Examiner*—Kathryne E. Shelborne
*Attorney, Agent, or Firm*—O'Keefe, Egan & Peterman

[57] ABSTRACT

This invention concerns a method useful for reducing odor where odoriferous amine-containing compound is present, comprising: applying an alkylene carbonate to a source of the amine-containing compound under conditions such that the alkylene carbonate forms a reaction product with odoriferous amine-containing compounds such that odor is reduced. Sources of such amine-containing compounds include chicken coops, dumps, land fills, cat litter, stagnant water, water treatment ponds and plants, garbage cans and dumpsters, dog kennels, zoos, rendering plants food processing plants, slaughter houses, wool plants, fish canneries (cleaning and processing plants), underground sewers, paper mills, paper processing, outhouses and toilets that have no running water, and public restrooms.

16 Claims, No Drawings

METHOD FOR CONTROLLING ODOR USING ALKYLENE CARBONATES

This application claims priority from U.S. Provisional Application Ser. No. 60/035,980, filed Jan. 22, 1997.

BACKGROUND OF INVENTION

This invention concerns the use of alkylene carbonates to reduce odor produced by amine-containing compounds.

A persistent problem in a variety of areas is the pungent odor which is present produced or exuded from urine, fecal matter and rotting organic material. A method for reducing such odors would be highly desirable. It would also be desirable if such a method employed active agents which where biodegradable and produced non-toxic reaction products.

SUMMARY OF INVENTION

This invention solves one or more of the problems and disadvantages described above.

In one broad respect, this invention is a method useful for reducing odor where odoriferous amine-containing compound is present, comprising: applying an alkylene carbonate to a source of the amine-containing compound under conditions such that the alkylene carbonate forms a reaction product with odoriferous amine-containing compounds such that odor is reduced. As used herein, odoriferous amine-containing compounds means any amine compound which may be produced by or expelled from urine, fecal matter and rotting organic material, such as urea. As used herein, waste excrement refers to solid fecal matter and urine, which expels amine-containing compounds thereby causing odor.

DETAILED DESCRIPTION OF THE INVENTION

The alkylene carbonates used in the practice of this invention contain from 2 to 10 carbon atoms. Representative examples of such alkylene carbonates include ethylene carbonate, propylene carbonate and butylene carbonate. Mixtures of two or more alkylene carbonates may be employed. A preferred alkylene carbonate is propylene carbonate.

The areas treated in the process of this invention are numerous, including chicken coops, dumps, land fills, cat litter, stagnant water, water treatment ponds and plants, garbage cans and dumpsters, dog kennels, zoos, rendering plants food processing plants, slaughter houses, wool plants, fish canneries (cleaning and processing plants), underground sewers, paper mills, paper processing, outhouses and toilets that have no running water, and public restrooms. The odoriferous amine-containing compounds which are abated through practice of this invention are also numerous. Representative examples of such compounds include urea and putricine.

The alkylene carbonates may be applied in a variety of ways. For example, propylene carbonate is a liquid at room temperature. It may be applied by spraying via any suitable pressurized spraying device. Spraying is continued until the target area is wetted. If odor persists, the propylene carbonate may be resprayed repeatedly until the odor smell is abated. Ethylene carbonate is a solid at room temperature, and can be applied in solid form onto the target area. Alternatively, the ethylene carbonate can be diluted with propylene carbonate or water and thereafter sprayed. The alkylene carbonates may generally be diluted with water as desired. However, it is contemplated that it would be most efficient to apply liquid alkylene carbonates or mixtures thereof by spraying the alkylene carbonate neat.

In some cases, the alkylene carbonate is applied prior to an area or material prior to being contaminated by materials which produce or expel amine-containing compounds. For example, cat litter can be sprayed with propylene carbonate prior to use or sale.

While not wishing to be bound by theory, it is believed that the alkylene carbonate reacts with amine-containing compounds in the fecal matter and urine to thereby reduce the level of amine and make the resulting product less volatile. Urea, for example, would be expected to react to form a carbamate. In the case of propylene carbonate, the urea would react to form a carbamate and propylene glycol. Propylene glycol is known to be non-toxic. Propylene carbonate itself is used in a variety of products such as cosmetics and skin care products, and is thus considered to be an environmentally safe product. Furthermore, it is known that propylene carbonate is biodegradable. It can be seen that propylene carbonate thus possesses a significant number of advantageous attributes which make it an ideal candidate in the method herein. Thus, even though ethylene carbonate is expected to be more reactive with amines, it is believed propylene carbonate would be preferred. Another advantage of the alkylene carbonates and by-products thereof is the low evaporation rate and relatively high boiling points, which means high flash point; hence, special handling is unnecessary.

In another embodiment, it is contemplated that alkylene carbonates can be introduced in a column. Air in a fish cannery, for example, can then be sent through the column whereby amine reacts with the alkylene carbonate to thereby reduce odor of the air. Alternatively, the air can be passed countercurrent to a descending spray of alkylene carbonate in a column.

In still another embodiment, general purification of air with bad odors can be accomplished in the practice of this invention. For instance, if the air smells bad because of acrid acid odors, acetic acid, vinegar, gases from pickle plants, amine odors or even smelly alcohols like butyl alcohol, one could purify the air by passing the contaminate containing air up flow in a packed column, alternatively at elevated temperatures, while passing an alkylene carbonate down flow in the column. The non-volatile liquid could be put into waste water treatment plants (e.g., ponds) and then released to the atmosphere.

What is claimed is:

1. A method useful for reducing odor where odoriferous amine-containing compound is present, comprising: applying an alkylene carbonate to a source selected from the group consisting of a chicken coop, dump, land fill, cat litter, stagnant water, water treatment pond, garbage can, dumpster, dog kennel, zoo, rendering plant, food processing plant, slaughter house, wool plant, fish cannery, underground sewer, paper mill, paper processing mill, outhouse, toilet that has no running water, or public restrooms, wherein the odoriferous amine-containing compound is present at the source, and wherein the alkylene carbonate forms a reaction product with the odoriferous amine-containing compounds such that odor is reduced.

2. The method of claim 1 wherein the alkylene carbonate is ethylene carbonate, propylene carbonate, butylene carbonate or mixture thereof.

3. The method of claim 1 wherein the alkylene carbonate is applied by spraying.

4. The method of claim 1 wherein the alkylene carbonate is applied by spraying using an air pressure driven spray apparatus.

5. The method of claim 1 wherein the alkylene carbonate is propylene carbonate.

6. A method useful for reducing odor where odoriferous amine-containing compound is present, comprising: applying a composition consisting of alkylene carbonate to a source of the amine-containing compound under conditions such that the alkylene carbonate forms a reaction product with odoriferous amine-containing compounds such that odor is reduced, wherein the source is a chicken coop, dump, land fill, cat litter, stagnant water, water treatment pond, garbage can, dumpster, dog kennel, zoo, rendering plant, food processing plant, slaughter house, wool plant, fish cannery, underground sewer, paper mill, paper processing mill, outhouse, toilet that has no running water, or public restrooms.

7. The method of claim 6 wherein the alkylene carbonate is ethylene carbonate, propylene carbonate, butylene carbonate or mixture thereof.

8. The method of claim 6 wherein the alkylene carbonate is applied by spraying.

9. The method of claim 6 wherein the alkylene carbonate is applied by spraying using an air pressure driven spray apparatus.

10. The method of claim 6 wherein the alkylene carbonate is propylene carbonate.

11. The method of claim 6 wherein the amine-containing compound includes urea.

12. A method useful for reducing odor where odoriferous amine-containing compound is present, comprising: applying an alkylene carbonate to a source of the amine-containing compound under conditions such that the alkylene carbonate forms a reaction product with odoriferous amine-containing compounds such that odor is reduced, wherein the source is a chicken coop, dump, land fill, cat litter, stagnant water, water treatment pond, garbage can, dumpster, dog kennel, zoo, rendering plant, food processing plant, slaughter house, wool plant, fish cannery, underground sewer, paper mill, paper processing mill, outhouse, toilet that has no running water, or public restrooms, wherein the amine-containing compound includes urea.

13. The method of claim 12 wherein the alkylene carbonate is ethylene carbonate, propylene carbonate, butylene carbonate or mixture thereof.

14. The method of claim 12 wherein the alkylene carbonate is applied by spraying.

15. The method of claim 12 wherein the alkylene carbonate is applied by spraying using an air pressure driven spray apparatus.

16. The method of claim 12 wherein the alkylene carbonate is propylene carbonate.

* * * * *